(12) United States Patent
McCord et al.

(10) Patent No.: US 9,791,434 B2
(45) Date of Patent: Oct. 17, 2017

(54) PAPER MICROFLUIDIC DEVICES FOR FORENSIC SEROLOGY

(71) Applicants: Bruce McCord, Miami, FL (US); George Duncan, Miami, FL (US); Ashley Wardlow, Miami, FL (US)

(72) Inventors: Bruce McCord, Miami, FL (US); George Duncan, Miami, FL (US); Ashley Wardlow, Miami, FL (US)

(73) Assignee: The Florida International University Board of Trustees, Miami, FL (US)

(*) Notice: Subject to any disclaimer, the term of this patent is extended or adjusted under 35 U.S.C. 154(b) by 0 days.

(21) Appl. No.: 15/257,238

(22) Filed: Sep. 6, 2016

(65) Prior Publication Data
US 2017/0067881 A1    Mar. 9, 2017

Related U.S. Application Data

(60) Provisional application No. 62/214,587, filed on Sep. 4, 2015.

(51) Int. Cl.
*B01L 3/00* (2006.01)
*G01N 33/50* (2006.01)
(Continued)

(52) U.S. Cl.
CPC ...... *G01N 33/521* (2013.01); *B01L 3/502707* (2013.01); *B01L 3/502715* (2013.01); *B01L 3/502746* (2013.01); *G01N 21/78* (2013.01); *G01N 33/52* (2013.01); *B01L 3/5027* (2013.01); *B01L 3/50273* (2013.01); *B01L 2200/10* (2013.01); *B01L 2200/12* (2013.01); *B01L 2200/16* (2013.01); *B01L 2300/0861* (2013.01); *B01L 2300/0864* (2013.01); *B01L 2300/12* (2013.01); *B01L 2300/126* (2013.01); *B01L 2300/165* (2013.01);
(Continued)

(58) Field of Classification Search
None
See application file for complete search history.

(56) References Cited

U.S. PATENT DOCUMENTS 6,372,514 B1 * 4/2002 Lee ................... G01N 33/521
                                                              422/412
2003/0119209 A1 * 6/2003 Kaylor ............. G01N 33/56911
                                                              436/548

(Continued)

OTHER PUBLICATIONS

Peters et al., "Simultaneous colorimetric detection of improvised explosive compounds using microfluidic paper-based analytical devices (µPADs)," Analytical Methods, 2015, pp. 63-70, vol. 7.*
(Continued)

*Primary Examiner* — Jennifer Wecker
(74) *Attorney, Agent, or Firm* — Saliwanchik, Lloyd & Eisenschenk (57) ABSTRACT

Paper microfluidic devices for the detection of bodily fluids are provided. Such devices can be used, for example, for detection of bodily fluids from or at crime scenes, including blood, saliva, semen, urine, feces, vaginal fluids, and perspiration. Detection can be performed using colorimetric reagents that react when placed in contact with the fluid of interest. A single device can be used to test for multiple bodily fluids at the same time.

13 Claims, 10 Drawing Sheets

(51) Int. Cl.

| | |
|---|---|
| G01N 33/48 | (2006.01) |
| G01N 33/34 | (2006.01) |
| G01N 33/52 | (2006.01) |
| G01N 21/78 | (2006.01) |
| G01N 1/28 | (2006.01) |
| G01N 21/75 | (2006.01) |
| G01N 1/00 | (2006.01) |
| G01N 21/77 | (2006.01) |
| G01N 35/00 | (2006.01) |
| G01N 21/84 | (2006.01) |

(52) U.S. Cl.
CPC .. *B01L 2400/0406* (2013.01); *G01N 21/8483* (2013.01); *G01N 33/346* (2013.01); *G01N 2021/752* (2013.01); *G01N 2021/7766* (2013.01); *G01N 2035/00108* (2013.01)

(56) References Cited

U.S. PATENT DOCUMENTS

| | | | | |
|---|---|---|---|---|
| 2007/0042444 | A1* | 2/2007 | Niskanen | B01L 3/5023 435/7.23 |
| 2008/0297169 | A1* | 12/2008 | Greenquist | B01L 3/502715 324/600 |
| 2009/0298191 | A1* | 12/2009 | Whitesides | G01N 33/523 436/164 |
| 2013/0280795 | A1* | 10/2013 | Dahl | G01N 33/5302 435/287.2 |
| 2014/0001058 | A1* | 1/2014 | Ghaffari | G01N 27/327 205/792 |
| 2016/0008813 | A1* | 1/2016 | Ledden | F04B 13/00 422/67 |
| 2016/0139102 | A1 | 5/2016 | McCord et al. | |

OTHER PUBLICATIONS

Martinez, Andres W., et al., "Patterned paper as a Platform for Inexpensive, Low-Volume, Portable Bioassays," Angew. Chem. Int. Ed. 2007, pp. 1318-1320, vol. 46.*

Bottegal, Megan et al., "Analysis of Ascorbic Acid-Based Black Powder Substitutes by High Performance Liquid Chromatography/Electrospray Ionization-Quadruple Time-of-Flight Mass Spectrometry (HPLC-ESI-QToFMS)," Rapid Communications in Mass Spectrometry, 2010, pp. 1377-1386, vol. 24, No. 9.

Carrilho, Emanuel, et al., Understanding wax printing: A Simple Micropatterning Process for Paper-Based Microfluidics, Analytical Chemistry, 2009, pp. 7091-7095, vol. 81, No. 16.

Collin, Olivier L., et al., "Fast Gas Chromatography of Explosive Compounds using a Pulsed Discharge Electron Capture Detector," Journal of Forensic Sciences, 2006, pp. 815-818, vol. 51, No. 4.

De Perre, Chloé et al., "Rapid and Specific Detection of Urea Nitrate and Ammonium Nitrate by Electrospray Ionization Time-of-flight Mass Spectrometry Using Infusion With Crown Ethers," Rapid Communications in Mass Spectrometry, 2011, pp. 154-162, vol. 26.

De Perre, Chloé, et al., "Trace Analysis of Urea Nitrate by Liquid Chromatography-UV/fluorescence," Forensic Science International, 2011, pp. 76-82, vol. 211, No. 1.

Doctor, Erika L., et al., "Comparison of Aggregating Agents for Surface-Enhanced Raman Analysis of Benzodiazepines," Analyst, 2013, pp. 5926-5932, vol. 138.

Doyle, Janet M., et al., "A Multicomponent Mobile Phase for Ion Chromatography Applied to the Separation of Anions from the Residue of Low Explosives," Analytical Chemistry, 2000, pp. 2303-2307, vol. 72, No. 10.

Doyle, Janet M., et al., "Novel Electrolyte for the Analysis of Cations in Low Explosive Residue by Capillary Electrophoresis," Journal of Chromatography B, 1998, pp. 105-111, vol. 714.

Dungchai, Wijitar, et al., "A Low-cost, Simple, and Rapid Fabrication Method for Paper-Based Microfluidics Using Wax Screen-Printing," Analyst, 2011, pp. 77-82, vol. 136.

Dungchai, Wijitar, et al., "Use of Multiple Colorimetric Indicators for Paper-Based Microfluidic Devices," Analytica Chimica Acta, 2010, pp. 227-233, vol. 674.

Heramb, Robert M., et al., "The Manufacture of Smokeless Powders and Their Forensic Analysis: A Brief Review," Forensic Science Communications, 2002, pp. 1-5, vol. 4, No. 2.

Hopper, Kristy G., et al., "A Novel Method for Analysis of Explosives Residue by Simultaneous Detection of Anions and Cations via Capillary Zone Electrophoresis," Talanta, 2005, pp. 304-312, vol. 67, No. 2.

Lahoda, Kristy G., et al., "A Survey of Background Levels of Explosives and Related Compounds in the Environment," Journal of Forensic Sciences, 2008, pp. 802-806, vol. 53, No. 4.

Li, Xiaokun, et al., "Gold Nanoparticle-Based Colorimetric Assay for Selective Detection of Aluminum Cation on Living Cellular Surfaces," Chem. Commun., 2010, pp. 988-990, vol. 46.

Lu, Yao, et al., "Rapid Prototyping of Paper-Based Microfluidics with Wax for Low-cost, Portable Bioassay," Electrophoresis, 2009, pp. 1-4, vol. 30.

Martinez, Andres W., et al., "Diagnostics for the Developing World: Microfluidic Paper-Based Analytical Devices," Analytical Chemistry, Jan. 2010, pp. 3-10, vol. 82, No. 1.

Mathis, John A., et al., "Gradient Reversed-Phase Liquid Chromatographic-Electrospray Ionization Mass Spectrometric Method for the Comparison of Smokeless Powders," Journal of Chromatography A, 2003, pp. 107-116, vol. 988.

Mathis, John A., et al., "The Analysis of High Explosives by Liquid Chromatography/Electrospray Ionization Mass Spectrometry: Multiplexed Detection of Negative Ion Adducts," Rapid Communications in Mass Spectrometry, 2005, pp. 99-104, vol. 19, No. 2.

McCord, Bruce et al., "Chromatography of Explosives: In Forensic Investigations of Explosives," 2nd Edition, Beveridge, A. D., Ed. Taylor and Francis, Boca Raton FL. 2012, pp. 585-620.

McCord, Bruce et al., "Forensic Analysis of Explosives using Ion Chromatographic Methods," Analytica Chimica Acta, 1994, pp. 43-56, vol. 288.

McCord, Bruce et al., "The Analysis and Characterization of TNT using Liquid Chromatography with Photodiode Array Detection," Journal of Forensic Sciences, 1992, pp. 1574-1584, vol. 37, No. 6.

Smith, Kelly D., et al., "Detection of Smokeless Powder Residue on Pipe Bombs by Micellar Electrokinetic Capillary Electrophoresis," Journal of Forensic Sciences, 1999, pp. 789-794, vol. 44, No. 4.

Tarvin, Megan, et al., "Analysis of Hydrogen Peroxide Field Samples by HPLC/FD and HPLC/ED in DC Mode," Forensic Science International, 2011, pp. 166-172, vol. 209, Nos. 1-3.

Tarvin, Megan, et al., "Optimization of Two Methods for the Analysis of Hydrogen Peroxide: High Performance Liquid Chromatography with Fluorescence Detection and High Performance Liquid Chromatography with Electrochemical Detection in Direct Current Mode," Journal of Chromatography A, 2010, pp. 7564-7572, vol. 1217, No. 48.

Thomas, Jennifer L., et al., "Separation and Detection of Smokeless Powder Additives by Ultra-high Performance Liquid Chromatography with Tandem Mass Spectrometry," (UPLC/MS/MS), Journal of Forensic Sciences, 2013, pp. 609-615, vol. 58, No. 3.

Wissinger, Chad E, et al., "A Reversed Phase HPLC Procedure for Smokeless Powder Comparison," Journal of Forensic Sciences, 2002, pp. 168-174, vol. 47, No. 1.

Martinez et al., "Diagnostics for the developing world: microfluidic paper-based analytical devices," Analytical Chemistry, Jan. 1, 2010, pp. 3-10, vol. 82, No. 1.

* cited by examiner

$NH_4^+ + 2\,[HgI_4]^{2-} + 4\,OH^- \rightarrow HgO\cdot Hg(NH_2)I + 7\,I^- + 3\,H_2O$

FIG. 13

PAPER MICROFLUIDIC DEVICES FOR FORENSIC SEROLOGY

CROSS-REFERENCE TO A RELATED APPLICATION

This application claims the benefit of U.S. Provisional Application Ser. No. 62/214,587, filed Sep. 4, 2015, which is hereby incorporated by reference herein in its entirety, including any figures, tables, or drawings.

BACKGROUND

Detection of bodily fluids, and the ability to distinguish between fluids, is very important in a variety of fields, including forensic serology. Forensic serology is the detection, classification, and study of various bodily fluids, in particular how they relate to a crime scene. Evidence from a crime scene is typically removed from the scene and transported to a forensic laboratory, where specialized examinations take place to identify unknown stains and further process them for DNA testing. Often, it is difficult to identify the presence and location of serological evidence.

Current methods of detection of biological fluids at a crime scene involve isolating the evidence and applying a series of individual tests to each sample in order to determine the type of bodily fluid present. These processes can waste precious sample, are inefficient, and can lead to running out of an item of evidence from a crime scene before all necessary testing takes place. Current forensic serology techniques also fail to provide long-term stability of test samples.

BRIEF SUMMARY

Embodiments of the subject invention provide paper microfluidic devices for the detection of bodily fluids, as well as methods of fabricating the same and methods of using the same. Paper microfluidic devices of the subject invention can be used, for example, for detection of bodily fluids from or at crime scenes. Bodily fluids that can be detected by the devices and methods of the subject invention include, but are not necessarily limited to, blood, saliva, semen, urine, feces, vaginal fluids, and perspiration. Detection can be performed using, for example, reagents (e.g., colorimetric reagents) that react when placed in contact with the fluid(s) of interest.

Embodiments of the subject invention can be fabricated from relatively inexpensive materials; thus, a paper microfluidic device according to the subject invention can perform multiple simultaneous analyses (e.g., 2, 5, 10, or more) at very low cost.

DETAILED DESCRIPTION

Embodiments of the subject invention provide paper microfluidic devices for the detection of bodily fluids, as well as methods of fabricating the same and methods of using the same. Paper microfluidic devices of the subject invention can be used, for example, for detection of bodily fluids from or at crime scenes. The identity of these fluids can be critical for forensic investigators searching for evidence at crime scenes. Bodily fluids (e.g. human bodily fluids) that can be detected by the devices and methods of the subject invention include, but are not necessarily limited to, blood, saliva, semen, urine, feces, vaginal fluids, and perspiration. Detection can be performed using, for example, reagents (e.g., colorimetric reagents) that react when placed in contact with the fluid(s) of interest. Embodiments of the subject invention can not only detect but also distinguish between different bodily fluids.

Figure 1:
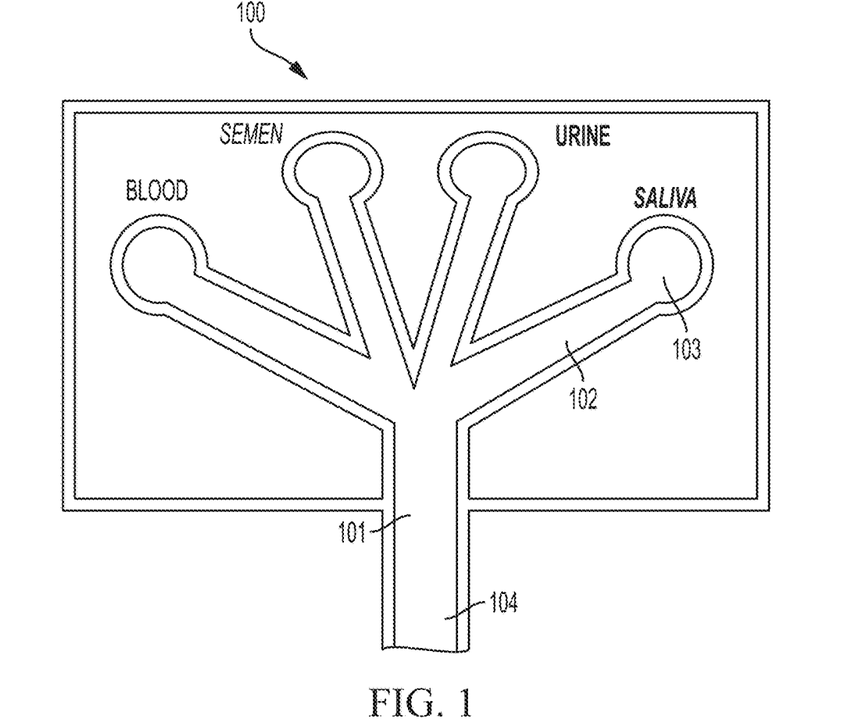
FIG. 1 shows a paper microfluidic device according to an embodiment of the subject invention.

FIG. 1 shows an image of a paper microfluidic device 100 according to an embodiment of the subject invention. Referring to FIG. 1, the device can include a central stem 101 and a plurality of branches or channels 102. The stem 101 can terminate in a tab 104, which can accept a test sample and can protrude from a chip (not shown). The protruding tab can be used to dip the microfluidic device into a test sample. The channels can be hydrophobic, though embodiments are not necessarily limited thereto. In many embodiments, the channels can be hydrophilic. The channels can be outlined by wax. At least one of the branches or channels can include a testing spot 103 (e.g., a well, such as a round well) at the end thereof such that the channel terminates in the testing spot. The well can include a testing reagent (e.g., a colorimetric testing reagent). In many embodiments, each branch or channel includes a testing spot (e.g., a well, such as a round well) at the end thereof such that the channel terminates in the testing spot, and each testing spot includes a testing reagent (e.g., a colorimetric testing reagent). Each testing spot can include a different testing reagent, which can be specific to a particular analyte.

Though FIG. 1 shows four branches and lists specific analytes, this is for demonstrative purposes only and should not be construed as limiting. A paper microfluidic device of the subject invention can have two, three, four, five, six, seven, eight, nine, 10, or more branches, and can perform a corresponding number of analyses on a single sample. These analyses can be performed simultaneously or essentially simultaneously (i.e., after providing a single sample to a device and allowing it to travel through channels to multiple testing points). Such a paper microfluidic device can be made of paper (e.g., chromatography paper) and wax, and can include small quantities of test reagents.

Testing reagents used with embodiments of the subject invention can be specific for certain bodily fluids, including but not necessarily limited to blood, saliva, semen, urine, feces, vaginal fluids, and perspiration. In many embodiments, each branch or channel of the paper microfluidic device includes a testing spot that includes a colorimetric testing reagent that is specific to a particular bodily fluid, and at least two of the testing spots having different testing reagents. Colorimetric testing reagents use physical and/or chemical properties of a chosen analyte such that the reagent reacts to give a visible color change when the analyte of interest is present.

It is possible to have a testing reagent repeated in more than one testing spot (or all testing spots), or to have multiple testing reagents, each repeated in more than one testing spot. In a particular embodiment, though, each testing spot has a testing reagent that is different from that of all other testing spots; in this way, a single sample can be tested for many bodily fluid analytes at the same time.

The sample to be tested can be provided on the paper microfluidic device (e.g., on the stem section thereof), and then it can move down the branches to the testing spots, which can have testing reagents. Capillary action or the natural wicking action of the paper as it draws up the liquid sample can take the place of a pump, and test reagents placed within the testing spots can give an immediate (or essentially immediate), visible color change when an analyte specific to a reagent is present.

Figure 2:
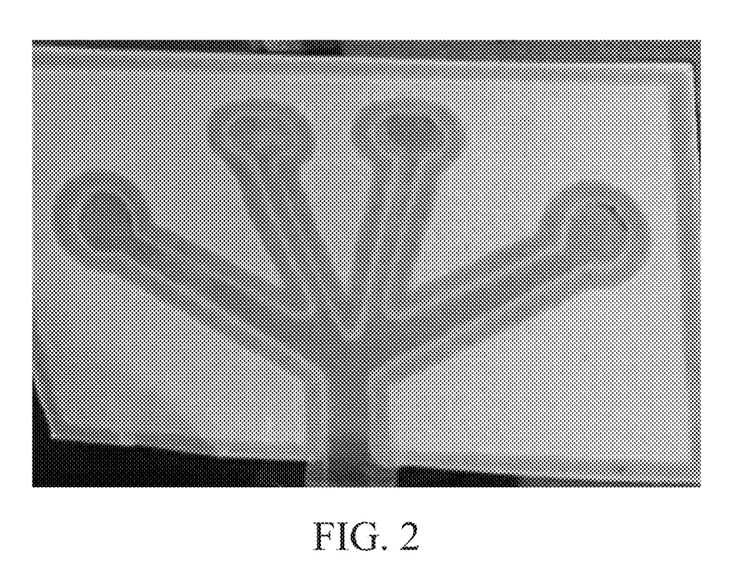
FIG. 2 shows a paper microfluidic device according to an embodiment of the subject invention.

FIG. 2 shows an image of a paper microfluidic device according to an embodiment of the subject invention. Referring to FIG. 2, each of the four branches present has a testing spot at the end thereof, and each testing spot has a different colorimetric testing reagent. A sample has been provided to the device, and it can be seen that some of the testing reagents have changed color, indicating the presence of particular bodily fluid analytes.

A sample to be tested can be dissolved in a solvent, if necessary, so that it can be in liquid form when tested. Examples of solvents that can be used include, but are not limited to, water, crown ethers, acetone, ethanol, methanol, dimethyl sulfoxide (DMSO), dimethylformaldehyde (DMF), and any combination thereof.

A paper microfluidic device can be fabricated by printing a pattern (e.g., a stem and a plurality of branches, each branch having a testing spot) on paper. The paper can be, for example, chromatographic paper, and the pattern can be printed using, for example, a wax printer such as a thermal wax printer, though embodiments are not necessarily limited thereto. In one embodiment, wax can be melted into the paper using a thermal laminator, and then reagents can be applied to the round wells at the end of each channel. Specific reagents for bodily fluids can be placed in the wells in the channels. When different testing reagents are used in different channels, a single unknown sample can be simultaneously tested for the presence of multiple bodily fluids. This process reduces the waste of a valuable sample by performing multiple tests on a single sample.

Certain aspects of fabricating the paper microfluidic device can be similar to those described in U.S. patent application Ser. No. 14/216,869 (filed Mar. 17, 2014) and U.S. Provisional Patent Application Ser. No. 61/794,955 (filed Mar. 15, 2013), each of which is incorporated herein by reference in its entirety.

In certain embodiments, multiple patterns can be created and printed onto a single sheet of chromatographic paper using a wax printer. The sheet (or sheets, if multiple sheets are printed) can be slipped into a cover (e.g., a sleeve of aluminum foil) and run through a laminator at a high temperature (e.g., 160° F. or higher) to bake the wax through the entire sheet. The individual paper microfluidic devices, which can be referred to as chips, can be cut (e.g., by hand with scissors such as sterilized scissors). In some embodiments, a strip of unwaxed paper can be left to be used for solvent and/or analyte delivery.

Reagents can be added directly to the paper microfluidic device. The reagents can be, for example, spotted onto the paper towards the ends of the channels. Certain reagents, such as sodium perborate and acid phosphatase spot reagent, can be made into a paste and lightly smeared into the testing spot and/or the middle of the channel. In one embodiment, the unwaxed tab of the chip, if present, can be inserted into water (e.g., distilled water), which can be, for example, in a small glass vial. The vial can have a small volume of, for example, 1000 µL or less of the water. The chip can be left in the water until the channels are saturated, and the chip can then be removed from the vial and left to dry.

Figure 10:
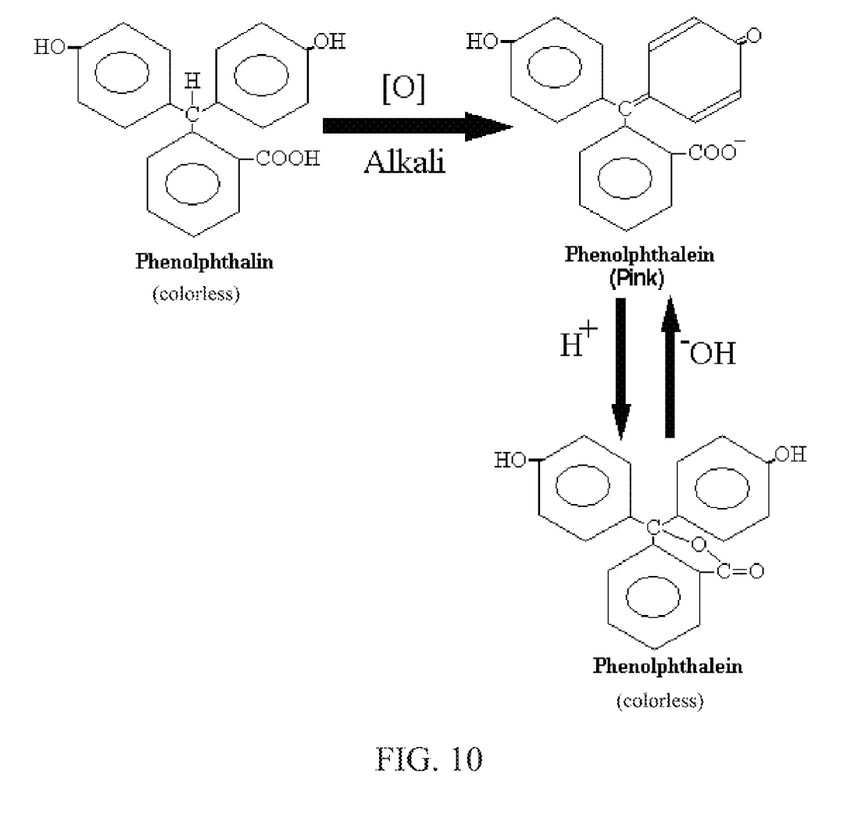
FIG. 10 shows the chemical formula of a test reagent that can be used according to an embodiment of the subject invention.
Figure 11:
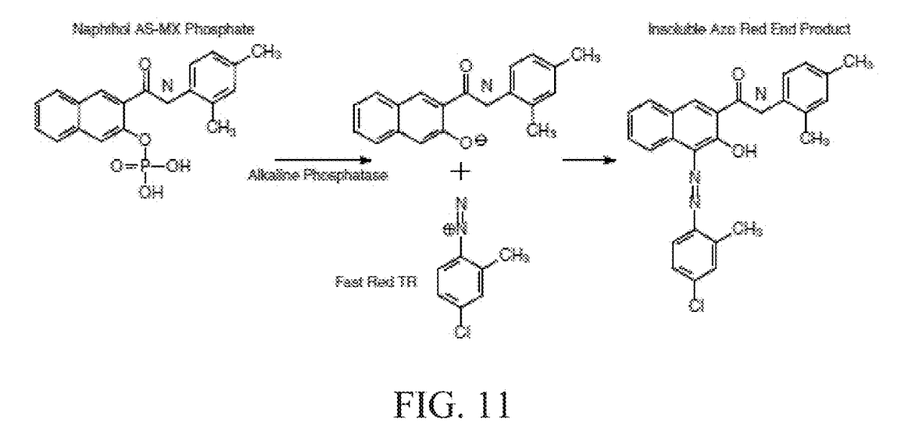
FIG. 11 shows the chemical formula of a test reagent that can be used according to an embodiment of the subject invention.
Figure 12:
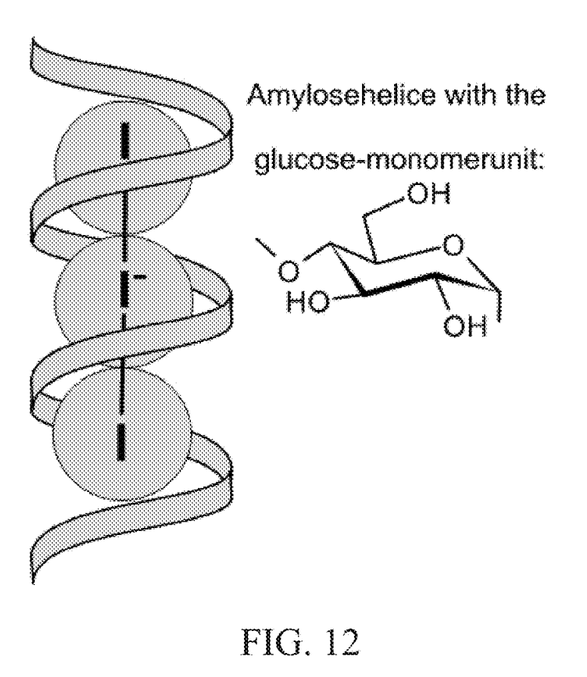
FIG. 12 shows the chemical formula of a test reagent that can be used according to an embodiment of the subject invention.
Figure 13:
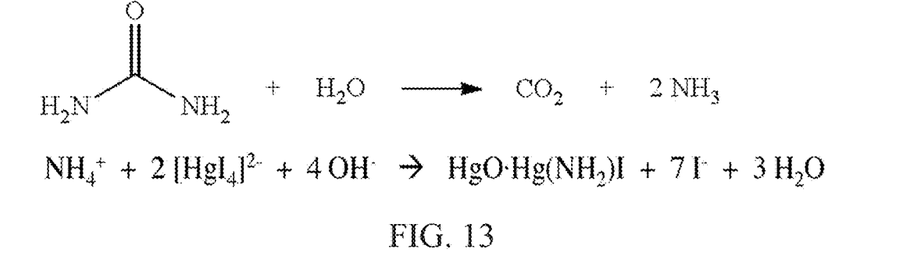
FIG. 13 shows the chemical formula of a test reagent that can be used according to an embodiment of the subject invention.

Table 1 lists examples of testing reagents that can be used with embodiments of the subject invention, along with their target bodily fluid analyte and the color produced if the target analyte is present. FIG. 10 shows the chemical formula for the phenolphthalein testing reagent, FIG. 11 shows the chemical formula for the acid phosphatase spot reagent, FIG. 12 shows the chemical formula for the starch/iodine testing reagent, and FIG. 13 shows the chemical formula for the urease/Nessler's testing reagent.

Based on the reagents listed in Table 1, the presumptive blood detection test involves the catalytic activity of the heme group in hemoglobin, a component of blood. The test utilizes the sodium perborate reagent to oxidize phenolphthalein (colorless) to phenolphthalein (colored). Also, acid phosphatase (AP) is a component of seminal fluid, along with other fluids such as vaginal fluids, feces, contraceptives, and plants. AP is present in semen in much greater quantities than these other fluids, though. The presence of AP in a stain or fluid can be visualized by the hydrolysis of a reagent containing alpha naphthyl phosphate and o-dianisdine (the AP Spot Reagent). When AP is present, alpha naphthyl phosphate will react to form phosphate and beta napthol, which in turn combines with o-dianisidine dye to produce a dark purple/pink color change. In addition, amylase is a component of saliva that can be detected by the addition of a starch followed by the addition of iodine solution. If amylase is not present, the iodine becomes trapped in the helical portions of the starch polymer, and the starch-iodine complex produces a purple color. The presence of amylase hydrolyzes starch to maltose and dextrins and therefore the iodine cannot bind to the starch molecules, resulting in a yellow color. Moreover, the urine detection test can rely on the use of urease, which breaks down urea and releases ammonia and carbon dioxide. The ammonia is then detected by an indicator, for example, Nessler's Reagent, where a dark blue/green color can be observed.

TABLE 1

Examples of testing reagents

| Colorimetric Reagent | Reactive Inorganic Element (analyte) | Color Produced |
|---|---|---|
| Phenolphthalein/Ethanol & Sodium Perborate | Blood | Bright Pink |
| Acid Phosphatase Spot Reagent | Semen | Dark Purple |
| Starch & Iodine | Saliva | Yellow |
| Urease & Nessler's Reagent | Urine | Dark Blue/Green |

The area of a paper microfluidic device according to embodiments of the subject invention can be less than 4.5 square centimeters ($cm^2$). The area of a paper microfluidic device according to embodiments of the subject invention can be less than, for example, 50 $cm^2$, 20 $cm^2$, 10 $cm^2$, 7 $cm^2$, 6.5 $cm^2$, 6 $cm^2$, 5 $cm^2$, 4.5 $cm^2$, 4.25 $cm^2$, 4.2 $cm^2$, 4.1 $cm^2$, 4 $cm^2$, 3.5 $cm^2$, 3 $cm^2$, 2 $cm^2$, 1 $cm^2$, or 0.5 $cm^2$. A paper microfluidic device according to embodiments of the subject invention can have a width and/or length (height) of, for example, 0.5 cm, 1 cm, 1.5 cm, 2 cm, 2.5 cm, 3 cm, 4 cm, 5 cm, 6 cm, 7 cm, 8 cm, 9 cm, or 10 cm.

Embodiments of the subject invention advantageously allow for a single sample to be tested for many bodily fluid analytes simultaneously (or essentially simultaneously) using a single paper microfluidic device. Devices of the subject invention also provide for long-term storage of testing reagents by stabilizing them on the paper.

Though paper substrates have been described in detail herein, other substrates that are planar and adsorbent can be used with embodiments of the subject invention.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

The subject invention includes, but is not limited to, the following exemplified embodiments.

Embodiment 1. A microfluidic device comprising:
a substrate;
one or more channels on the substrate;
one or more test spots on each of the channels; and
one or more test reagents in each of the one or more test spots;
wherein the one or more test reagents are suitable for testing (or configured to test) for bodily fluids.

Embodiment 2. The microfluidic device of Embodiment 1, wherein the substrate is a paper substrate.

Embodiment 3. The microfluidic device of any of Embodiments 1 to 2, wherein one or more of the channels is hydrophobic.

Embodiment 4. The microfluidic device of any of Embodiments 1 to 3, wherein one or more of the channels is hydrophilic.

Embodiment 5. The microfluidic device of any of Embodiments 1 to 4, including a first channel, having a first test spot and a first reagent, wherein the first reagent is suitable for testing (or configured to test) for blood.

Embodiment 6. The microfluidic device of any of Embodiments 1 to 5, including a second channel, having a second test spot and a second reagent, wherein the second reagent is suitable for testing (or configured to test) for semen.

Embodiment 7. The microfluidic device of any of Embodiments 1 to 6, including a third channel, having a third test spot and a third reagent, wherein the third reagent is suitable for testing (or configured to test) for urine.

Embodiment 8. The microfluidic device of any of Embodiments 1 to 7, including a fourth channel, having a fourth test spot and a fourth reagent, wherein the fourth reagent is suitable for testing (or configured to test) for saliva.

Embodiment 9. The microfluidic device of any of Embodiments 1 to 8, including a fifth channel, having a fifth test spot and a fifth reagent, wherein the fifth reagent is suitable for testing (or configured to test) for feces.

Embodiment 10. The microfluidic device of any of Embodiments 1 to 9, including a sixth channel, having a sixth test spot and a sixth reagent, wherein the sixth reagent is suitable for testing (or configured to test) for vaginal fluid.

Embodiment 11. The microfluidic device of any of Embodiments 1 to 10, including a seventh channel, having a seventh test spot and a seventh reagent, wherein the seventh reagent is suitable for testing (or configured to test) for perspiration.

Embodiment 12. The microfluidic device of any of Embodiments 1 to 11, further comprising a central stem that feeds into the one or more channels.

Embodiment 13. The microfluidic device of any of Embodiments 1 to 12, further comprising wax on a surface of the substrate.

Embodiment 14. The microfluidic device of any of Embodiments 1 to 13, further comprising wax baked into or impregnated into the substrate.

Embodiment 15. The microfluidic device of any of Embodiments 1 to 14, wherein a chip of the substrate has a maximum length or width of 5 centimeters.

Embodiment 16. The microfluidic device of any of Embodiments 1 to 15, wherein the substrate is suitable for providing capillary action to move a sample or sample solution through the one or more channels.

Embodiment 17. The microfluidic device of any of Embodiments 1 to 16, further comprising a tab at an end of the central stem, wherein the tab is suitable for receiving a test sample.

Embodiment 18. The microfluidic device of any of Embodiments 1 to 17, wherein the tab protrudes from the chip.

Embodiment 101. A method of fabricating a microfluidic device, the method comprising:
providing a substrate;
providing a pattern on the substrate including one or more channels, and one or more test spots on each of the channels; and
providing one or more test reagents in each of the one or more test spots;
wherein the one or more test reagents are suitable for testing (or configured to test) for bodily fluids.

Embodiment 102. The microfluidic device of Embodiment 101, wherein the substrate is a paper substrate or chromatographic paper.

Embodiment 103. The method of fabricating a microfluidic device of any of Embodiments 101 to 102, wherein one or more of the channels is hydrophobic.

Embodiment 104. The method of fabricating a microfluidic device of any of Embodiments 101 to 103, wherein one or more of the channels is hydrophilic.

Embodiment 105. The method of fabricating a microfluidic device of any of Embodiments 101 to 104, including providing a first channel, having a first test spot and a first reagent, wherein the first reagent is suitable for testing (or configured to test) for blood.

Embodiment 106. The method of fabricating a microfluidic device of any of Embodiments 101 to 105, including providing a second channel, having a second test spot and a second reagent, wherein the second reagent is suitable for testing (or configured to test) for semen.

Embodiment 107. The method of fabricating a microfluidic device of any of Embodiments 101 to 106, including providing a third channel, having a third test spot and a third reagent, wherein the third reagent is suitable for testing (or configured to test) for urine.

Embodiment 108. The method of fabricating a microfluidic device of any of Embodiments 101 to 107, including providing a fourth channel, having a fourth test spot and a fourth reagent, wherein the fourth reagent is suitable for testing (or configured to test) for saliva.

Embodiment 109. The method of fabricating a microfluidic device of any of Embodiments 101 to 108, including providing a fifth channel, having a fifth test spot and a fifth reagent, wherein the fifth reagent is suitable for testing (or configured to test) for feces.

Embodiment 110. The method of fabricating a microfluidic device of any of Embodiments 101 to 109, including providing a sixth channel, having a sixth test spot and a sixth reagent, wherein the sixth reagent is suitable for testing (or configured to test) for vaginal fluid.

Embodiment 111. The method of fabricating a microfluidic device of any of Embodiments 101 to 110, including providing a seventh channel, having a seventh test spot and a seventh reagent, wherein the seventh reagent is suitable for testing (or configured to test) for perspiration.

Embodiment 112. The method of fabricating a microfluidic device of any of Embodiments 101 to 111, further comprising providing a central stem that feeds into the one or more channels.

Embodiment 113. The method of fabricating a microfluidic device of any of Embodiments 101 to 112, wherein the pattern is a wax pattern.

Embodiment 114. The method of fabricating a microfluidic device of any of Embodiments 101 to 113, further comprising baking wax or impregnating wax into the substrate.

Embodiment 115. The method of fabricating a microfluidic device of any of Embodiments 101 to 114, wherein a chip of the substrate has a maximum length or width of 5 centimeters.

Embodiment 116. The method of fabricating a microfluidic device of any of Embodiments 101 to 114, wherein the pattern is provided on the substrate using a wax printer.

Embodiment 201. A method using the microfluidic device of any of Embodiments 1 to 18 comprising introducing a bodily fluid sample to the microfluidic device.

Embodiment 202. The method using the microfluidic device of Embodiment 201, further comprising introducing the bodily fluid sample into a solvent.

Embodiment 203. The method using the microfluidic device of Embodiment 202, wherein the solvent includes one or more of water, crown ethers, acetone, ethanol, methanol, dimethyl sulfoxide (DMSO), dimethylformaldehyde (DMF), or any combination thereof.

Embodiment 210. A microfluidic device comprising:
a paper substrate;
a wax pattern on the paper substrate and comprising a plurality of channels and a central stem that feeds into the plurality of channels;
a plurality of test spots on the channels, respectively; and
a test reagent in each test spot;
the one or more test reagents being suitable for testing for bodily fluids; and
the plurality of channels and the plurality of test spots comprising at least two of the following:
  a first channel, having a first test spot and a first test reagent suitable for testing for blood;
  a second channel, having a second test spot and a second test reagent suitable for testing for semen;
  a third channel, having a third test spot and a third test reagent suitable for testing for urine;
  a fourth channel, having a fourth test spot and a fourth test reagent suitable for testing for saliva;
  a fifth channel, having a fifth test spot and a fifth test reagent suitable for testing for feces;
  a sixth channel, having a sixth test spot and a sixth test reagent suitable for testing for vaginal fluid; and
  a seventh channel, having a seventh test spot and a seventh test reagent suitable for testing for perspiration.

Embodiment 211. The microfluidic device according to Embodiment 210, wherein the plurality of channels and the plurality of test spots comprises at least four of the following:
  a first channel, having a first test spot and a first test reagent suitable for testing for blood;
  a second channel, having a second test spot and a second test reagent suitable for testing for semen;
  a third channel, having a third test spot and a third test reagent suitable for testing for urine;
  a fourth channel, having a fourth test spot and a fourth test reagent suitable for testing for saliva;
  a fifth channel, having a fifth test spot and a fifth test reagent suitable for testing for feces;
  a sixth channel, having a sixth test spot and a sixth test reagent suitable for testing for vaginal fluid; and
  a seventh channel, having a seventh test spot and a seventh test reagent suitable for testing for perspiration.

EXAMPLE 1

Figure 3:
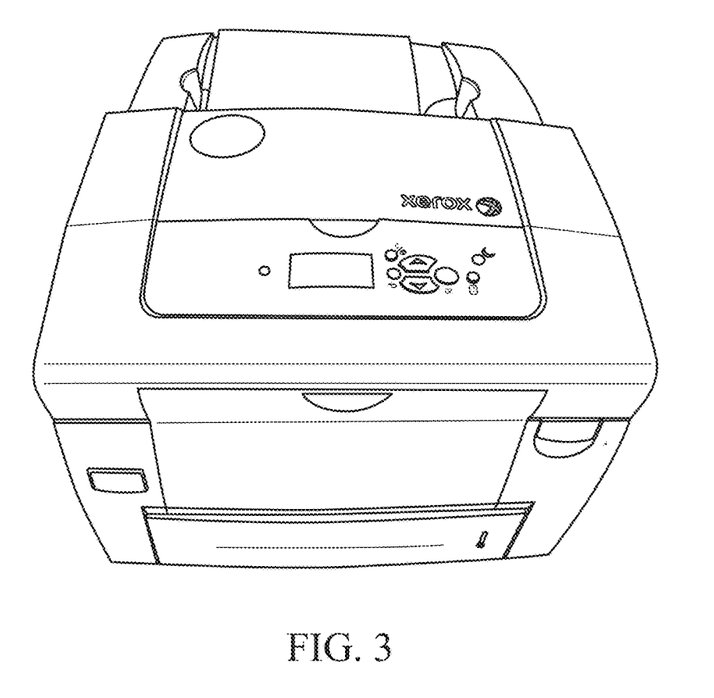
FIG. 3 shows an image of a wax printer used in the fabrication of a paper microfluidic device.
Figure 4:
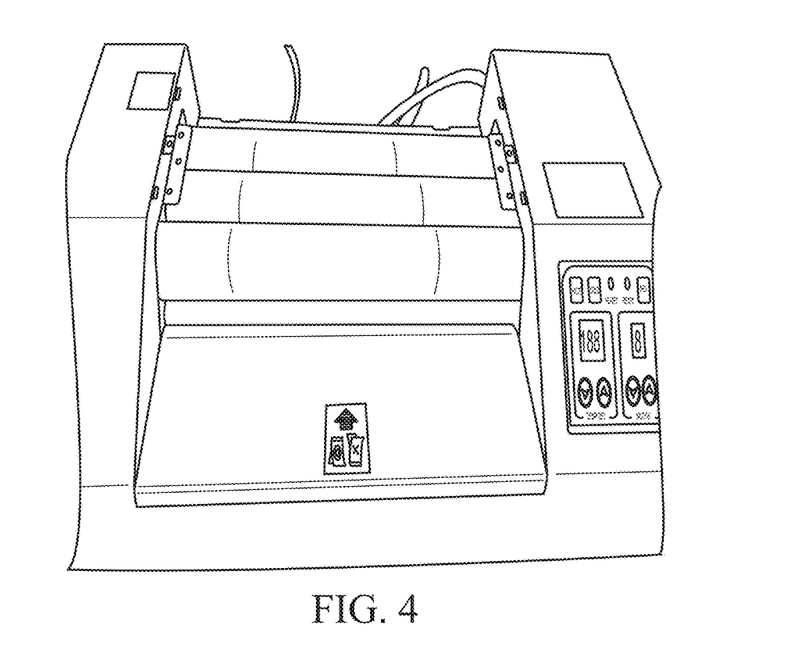
FIG. 4 shows an image of a wax printer used in the fabrication of a paper microfluidic device.

Patterns for chips of a paper microfluidic device were designed on MICROSOFT PAINT and then printed out on chromatographic paper using a wax printer. The pattern used is shown in FIG. 1. FIG. 3 shows an image of the wax printer used. The sheets were then slipped into sleeves of aluminum foil and run through a laminator at a temperature of 160° F. to bake the wax through the entire sheet. FIG. 4 shows an image of the laminator used. The individual chips were cut by hand with sterilized scissors, with a strip of unwaxed paper left to allow for solvent and analyte delivery. The reagents listed in Table 1 were added directly to the paper of an individual chip, one testing reagent or reagent combination in each of the four testing spots. Sodium perborate and acid phosphatase spot reagent were made into a paste and lightly smeared into the left-most testing spot and the channel that was second from the left, respectively. The saliva reagent combination was spotted onto the right-most testing spot, the urine reagent combination was spotted onto the testing spot that was second from the right, and the remainder of the blood testing reagent combination was spotted onto the left-most testing spot. The unwaxed tab of the chip was inserted into a small glass vial containing 1000 µL of distilled water and left to run until the channels were saturated. The chip was then removed from the vial and left to dry.

Figure 5:
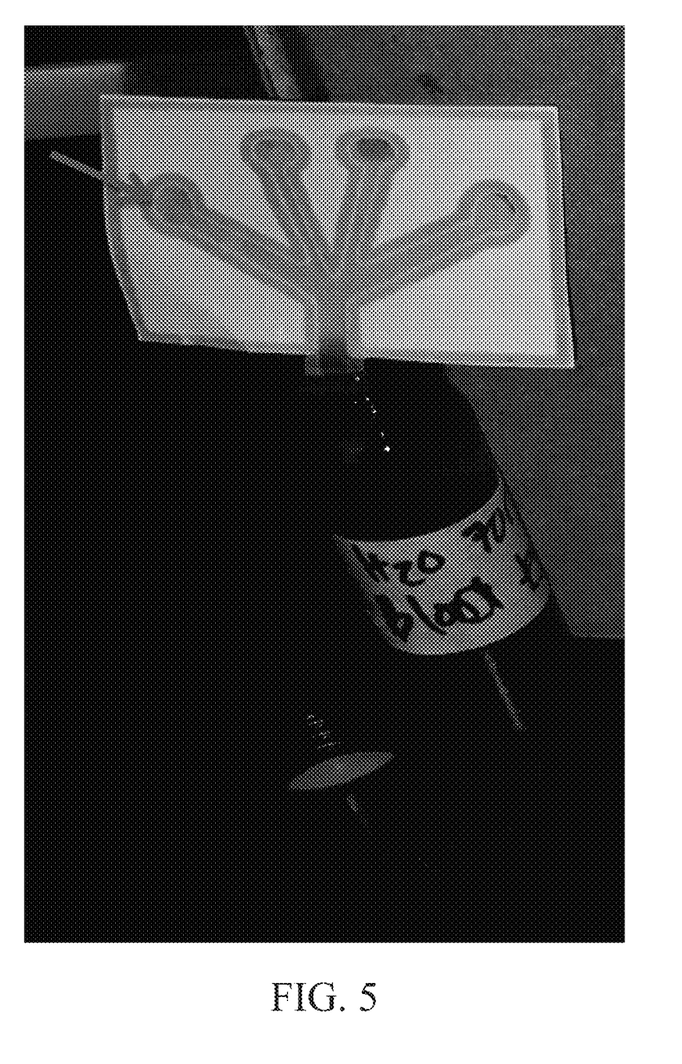
FIG. 5 shows a paper microfluidic device according to an embodiment of the subject invention.

A sample containing blood was provided to the chip by placing the unwaxed tab of the chip in a vial containing the sample. Referring to FIG. 5, it can be seen that the left-most testing spot indicates the presence of blood by changing to bright pink.

EXAMPLE 2

Figure 6:
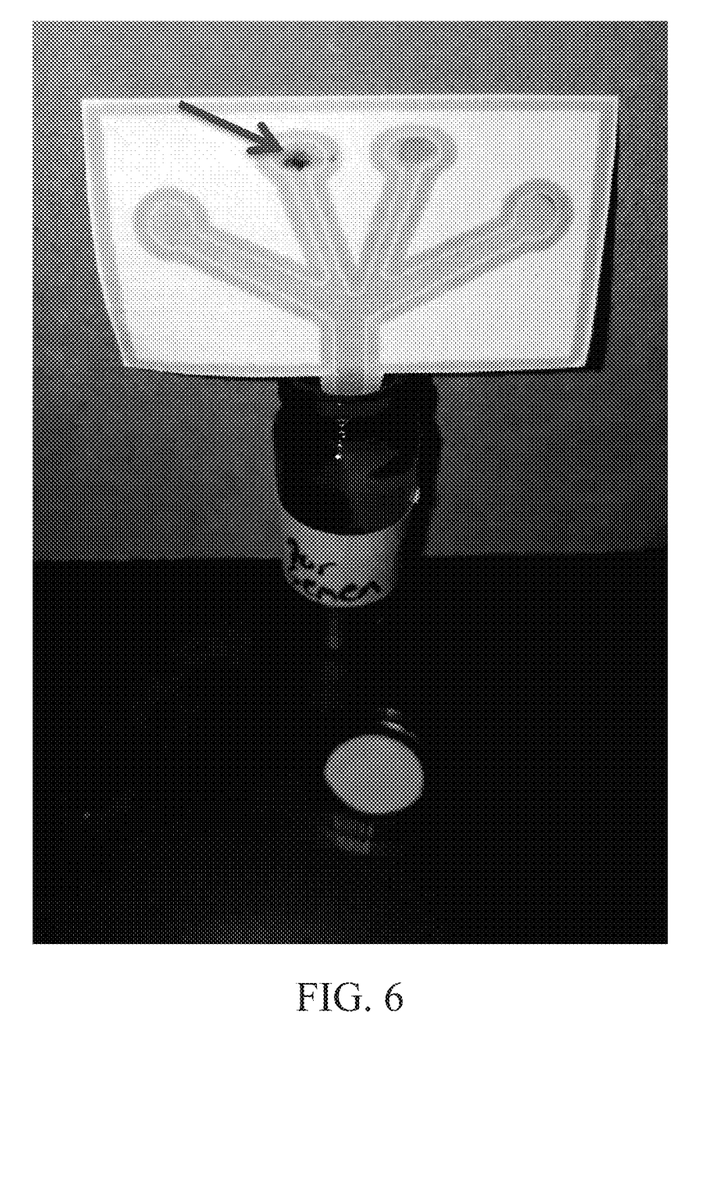
FIG. 6 shows a paper microfluidic device according to an embodiment of the subject invention.

The paper microfluidic device chip as in Example 1 was prepared, and a sample containing semen was provided to the chip by placing the unwaxed tab of the chip in a vial containing the sample. Referring to FIG. 6, it can be seen that the testing spot second from the left indicates the presence of blood by changing to dark purple.

EXAMPLE 3

Figure 7:
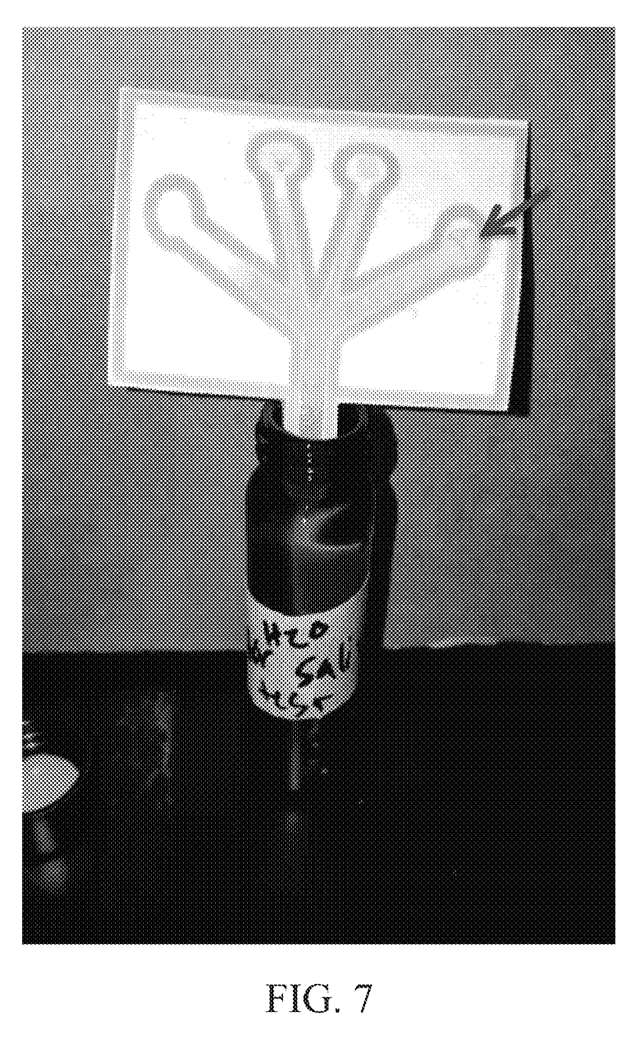
FIG. 7 shows a paper microfluidic device according to an embodiment of the subject invention.

The paper microfluidic device chip as in Example 1 was prepared, and a sample containing saliva was provided to the chip by placing the unwaxed tab of the chip in a vial containing the sample. Referring to FIG. 7, it can be seen that the right-most testing spot indicates the presence of saliva by changing to yellow.

EXAMPLE 4

Figure 8:
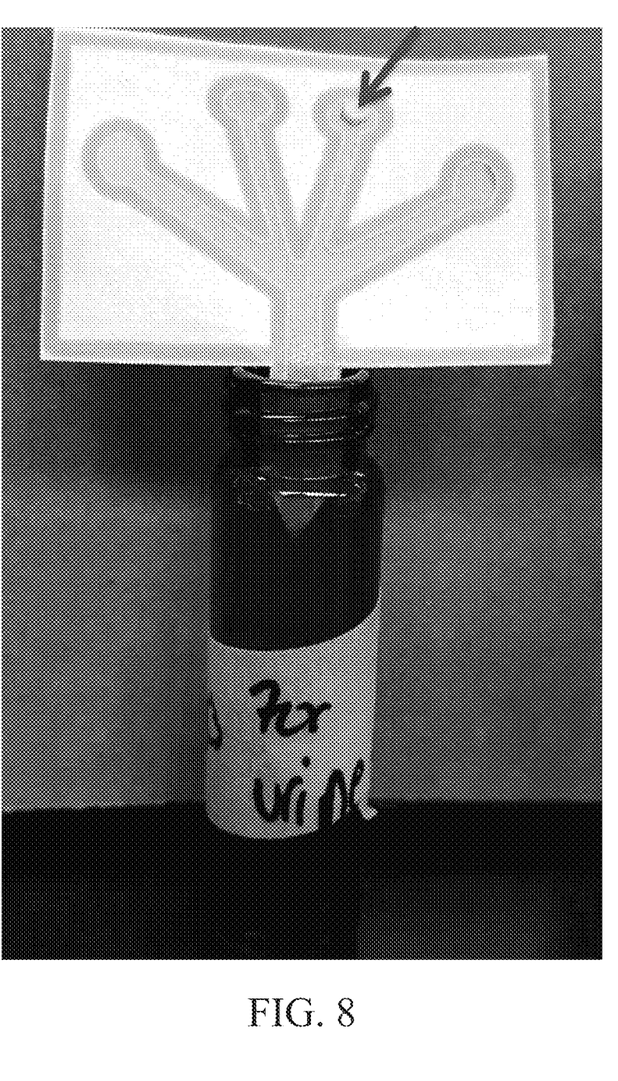
FIG. 8 shows a paper microfluidic device according to an embodiment of the subject invention.

A paper microfluidic device chip such as that in Example 1 was prepared, and a sample containing urine was provided to the chip by placing the unwaxed tab of the chip in a vial containing the sample. Referring to FIG. 8, it can be seen that the testing spot second from the right indicates the presence of urine by changing to a dark blue/green color.

EXAMPLE 5

Figure 9:
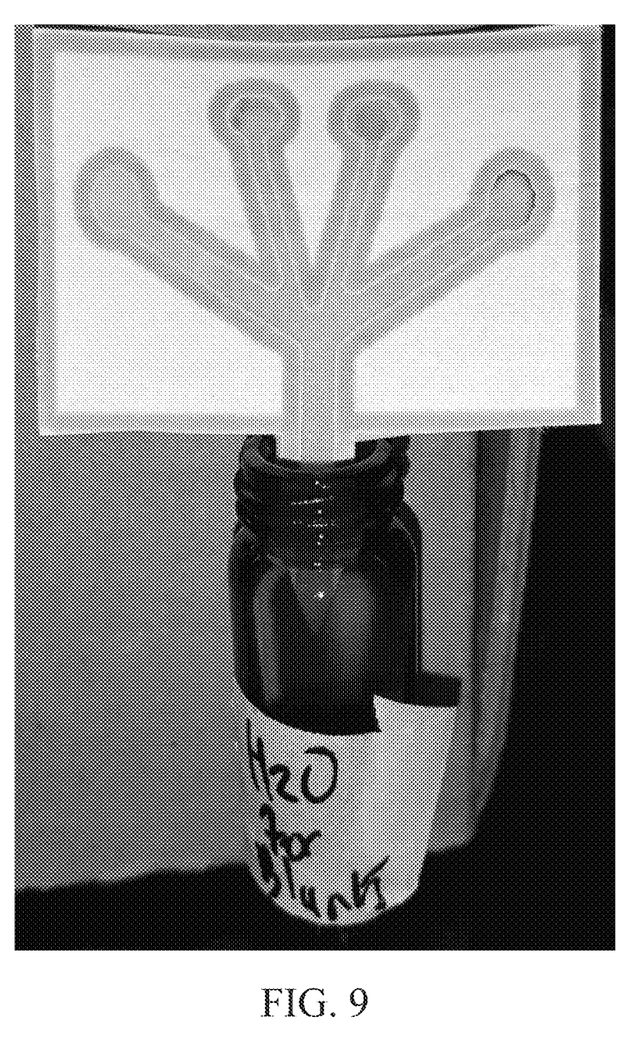
FIG. 9 shows a paper microfluidic device according to an embodiment of the subject invention.

A paper microfluidic device chip such as that in Example 1 was prepared, and a sample containing no blood, semen, saliva, or urine ("blank sample") was provided to the chip by placing the unwaxed tab of the chip in a vial containing the sample. Referring to FIG. 9, it can be seen that none of the testing spots indicated the presence of an analyte (i.e., no false positive occurred).

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

Martinez, A. W.; Phillips, S. T.; Whitesides, G. M.; Carrilho, E.; *Anal Chem.*; 82(1):3-10; 2010.
Forensic Science: An Introduction to Scientific and Investigative Techniques; Stuart H. James, Jon J. Nordby, Suzanne Bell; (Eds); Talyor and Francis; Boca Raton; 2014.
Peters, K. L.; Corbin, I.; Kaufman, L. M.; Zreibe, K.; Blanes, L.; McCord, B.; *Analytical methods;* 7:63-70; 2015.
U.S. patent application Ser. No. 14/216,869 (filed Mar. 17, 2014).
U.S. Provisional Patent Application Ser. No. 61/794,955 (filed Mar. 15, 2013).

What is claimed is:

1. A microfluidic device comprising:
   a substrate;
   one or more channels on the substrate;
   one or more test spots on the channels, respectively;
   one or more colorimetric test reagents in each test spot;
   wax on the substrate, said wax outlining and surrounding each channel of the one or more channels except a portion of each channel that receives a test sample when in use; and
   a tab protruding from the substrate and comprising a proximal end and a distal end opposite to the proximal end, said tab configured such that the distal end contacts a test sample when in use,
   the distal end of the tab being free from wax,
   the one or more colorimetric test reagents being suitable for testing for bodily fluids,
   the plurality of channels and the plurality of test spots comprising at least one of the following:
      a first channel, having a first test spot and a first colorimetric test reagent suitable for testing for feces;
      a second channel, having a second test spot and a second colorimetric test reagent suitable for testing for vaginal fluid;
      a third channel, having a third test spot and a third colorimetric test reagent suitable for testing for perspiration, and
   the plurality of channels and the plurality of test spots further comprising:
      a fourth channel, having a fourth test spot and a fourth colorimetric test reagent that comprises phenolphthalein, ethanol, and sodium perborate for testing for blood;
      a fifth channel, having a fifth test spot and a fifth colorimetric test reagent that comprises acid phosphatase spot reagent for testing for semen;
      a sixth channel, having a sixth test spot and a sixth colorimetric test reagent that comprises starch and iodine for testing for saliva; and
      a seventh channel, having a seventh test spot and a seventh colorimetric test reagent that comprises urease and Nessler's reagent for testing for urine.

2. The microfluidic device according to claim 1, the one or more channels being hydrophobic.

3. The microfluidic device according to claim 1, the substrate being a paper substrate.

4. The microfluidic device according to claim 1, further comprising a central stem that feeds into the two or more channels.

5. The microfluidic device according to claim 4, the wax being on a top surface of the substrate.

6. The microfluidic device according to claim 4, the wax being baked into or impregnated into the substrate.

7. A method of fabricating a microfluidic device, the method comprising:
   providing a substrate;
   providing a pattern on the substrate including one or more channels, and one or more test spots on the channels, respectively;

providing wax on the substrate, said wax outlining and surrounding each channel of the one or more channels except a portion of each channel that receives a test sample when in use;

providing a tab protruding from the substrate and comprising a proximal end and a distal end opposite to the proximal end, said tab configured such that the distal end contacts a test sample when in use; and providing one or more colorimetric test reagents in each test spot;

the one or more colorimetric test reagents being suitable for testing for bodily fluids, the distal end of the tab being free from wax, the plurality of channels and the plurality of test spots comprising at least one of the following:
- a first channel, having a first test spot and a first colorimetric test reagent suitable for testing for feces;
- a second channel, having a second test spot and a second colorimetric test reagent suitable for testing for vaginal fluid;
- a third channel, having a third test spot and a third colorimetric test reagent suitable for testing for perspiration, and the plurality of channels and the plurality of test spots further comprising:
- a fourth channel, having a fourth test spot and a fourth colorimetric test reagent that comprises phenolphthalein, ethanol, and sodium perborate for testing for blood;
- a fifth channel, having a fifth test sot and a fifth colorimetric test reagent that comprises acid phosphatase spot reagent for testing for semen;
- a sixth channel, having a sixth test spot and a sixth colorimetric test reagent that comprises starch and iodine for testing for saliva; and
- a seventh channel, having a seventh test spot and a seventh colorimetric test reagent that comprises urease and Nessler's reagent for testing for urine.

8. The method of fabricating a microfluidic device according to claim 7, the substrate being a paper substrate.

9. The method of fabricating a microfluidic device according to claim 8, the one or more channels being hydrophobic.

10. The method of fabricating a microfluidic device according to claim 8, the step of providing wax on the substrate comprising baking wax or impregnating wax into the substrate.

11. The method of fabricating a microfluidic device according to claim 7, the plurality of channels and the plurality of test spots comprising at least two of the first channel, the second channel, and the third channel.

12. The method of fabricating a microfluidic device according to claim 7, the plurality of channels and the plurality of test spots comprising all three of the first channel, the second channel, and the third channel.

13. A microfluidic device comprising:

a paper substrate;

a wax pattern on the paper substrate and comprising a plurality of channels and a central stem that feeds into the plurality of channels, the wax of said wax pattern outlining and surrounding each channel of the plurality of channels except a portion of each channel that receives a test sample when in use;

a tab protruding from the paper substrate and comprising a proximal end and a distal end opposite to the proximal end, said tab configured such that the distal end contacts a test sample when in use;

a plurality of test spots on the channels, respectively; and a colorimetric test reagent in each test spot;

the distal end of the tab being free from wax;

each colorimetric test reagent being suitable for testing for bodily fluids;

the plurality of channels and the plurality of test spots comprising the following:
- a first channel, having a first test spot and a first colorimetric test reagent suitable for testing for blood;
- a second channel, having a second test spot and a second colorimetric test reagent suitable for testing for semen;
- a third channel, having a third test spot and a third colorimetric test reagent suitable for testing for urine;
- a fourth channel, having a fourth test spot and a fourth colorimetric test reagent suitable for testing for saliva;
- a fifth channel, having a fifth test spot and a fifth colorimetric test reagent suitable for testing for feces;
- a sixth channel, having a sixth test spot and a sixth colorimetric test reagent suitable for testing for vaginal fluid; and
- a seventh channel, having a seventh test spot and a seventh colorimetric test reagent suitable for testing for perspiration, the first colorimetric test reagent comprising phenolphthalein, ethanol, and sodium perborate for testing for blood;

the second colorimetric test reagent comprising acid phosphatase spot reagent for testing for semen;

the third colorimetric test reagent comprising urease and Nessler's reagent for testing for urine; and the fourth colorimetric test reagent comprising starch and iodine for testing for saliva.

* * * * *